United States Patent
Izumiya et al.

(10) Patent No.: US 7,938,124 B2
(45) Date of Patent: May 10, 2011

(54) APPLIED FLAVORING-MATERIAL INSPECTION DEVICE AND CIGARETTE MAKING MACHINE PROVIDED WITH SAME

(75) Inventors: Takafumi Izumiya, Tokyo (JP); Shinzo Kida, Tokyo (JP)

(73) Assignee: Japan Tobacco Inc., Tokyo (JP)

(*) Notice: Subject to any disclaimer, the term of this patent is extended or adjusted under 35 U.S.C. 154(b) by 259 days.

(21) Appl. No.: 11/184,789

(22) Filed: Jul. 20, 2005

(65) Prior Publication Data
US 2005/0252516 A1 Nov. 17, 2005

Related U.S. Application Data (63) Continuation of application No. PCT/JP2004/000392, filed on Jan. 20, 2004.

(30) Foreign Application Priority Data

Jan. 21, 2003 (JP) ................................ 2003-012478

(51) Int. Cl.
*A24C 5/00* (2006.01)
*A24C 5/32* (2006.01)
*A24C 5/38* (2006.01)

(52) U.S. Cl. ........................................ 131/280; 131/908
(58) Field of Classification Search .................. 131/280, 131/908
See application file for complete search history.

(56) References Cited

U.S. PATENT DOCUMENTS

| | | | | |
|---|---|---|---|---|
| 4,845,374 A | * | 7/1989 | White et al. ................ | 250/559.4 |
| 5,022,950 A | * | 6/1991 | Ingalls et al. ............... | 156/361 |
| 5,110,213 A | * | 5/1992 | Seymour ..................... | 356/445 |
| 5,156,169 A | * | 10/1992 | Holmes et al. .............. | 131/60 |
| 5,531,233 A | * | 7/1996 | Oglesby et al. .............. | 131/69 |
| 6,020,969 A | * | 2/2000 | Struckhoff et al. .......... | 356/430 |
| 2003/0131860 A1 | * | 7/2003 | Ashcraft et al. ............. | 131/365 |

FOREIGN PATENT DOCUMENTS

| | | |
|---|---|---|
| JP | 1-291145 A | 11/1989 |
| JP | 6-95921 B2 | 11/1994 |
| JP | 11-56335 A | 2/1999 |
| JP | 2938067 B1 | 8/1999 |
| JP | 2001-509366 A | 7/2001 |
| RU | 2000103214 A | 12/2001 |
| WO | WO 01/72155 A1 | 10/2001 |

* cited by examiner

*Primary Examiner* — Matthew J Daniels
*Assistant Examiner* — Cynthia Szewczyk
(74) *Attorney, Agent, or Firm* — Birch, Stewart, Kolasch & Birch, LLP (57) ABSTRACT

An applied flavoring-material inspecting device suitable to inspect that a flavoring material containing a fluorescent substance is applied on cigarette wrapping paper evenly and in a proper amount. The inspecting device comprises a light source (10) for casting ultraviolet light onto a flavoring-material application surface of cigarette wrapping paper on which a flavoring material with a fluorescent substance added or containing a fluorescent substance is applied, a camera (20) for obtaining an image of the flavoring-material application surface from fluorescence radiated due to the ultraviolet light, and an image processing means (30) for detecting an area of a fluorescence irradiation region in an image for inspection obtained by digitizing the image obtained by the camera and determining an applying state of the flavoring material applied on the cigarette wrapping paper, from the area of the fluorescence irradiation region.

12 Claims, 4 Drawing Sheets

APPLIED FLAVORING-MATERIAL INSPECTION DEVICE AND CIGARETTE MAKING MACHINE PROVIDED WITH SAME

This application is a Continuation of co-pending PCT International Application No. PCT/JP2004/000392 filed on Jan. 20, 2004, which designated the United States, and on which priority is claimed under 35 U.S.C. §120. This application also claims priority under 35 U.S.C. §119(a) on Patent Application No(s). 2003-12478 filed in Japan on Jan. 21, 2003. The entire contents of each of the above documents is hereby incorporated by reference.

TECHNICAL FIELD

This invention relates to an applied flavoring of a flavoring-material applied on cigarette wrapping paper and a cigarette making machine provided with an applied flavoring-material inspection device.

BACKGROUND ART

Generally, a cigarette is a rod of cut tobacco wrapped in wrapping paper, where the opposite sides of the wrapping paper are stuck together with seam glue. In order to improve the taste of such cigarettes, it is known to add a flavoring material to cut tobacco. Recently, adding a flavoring material to seam glue in advance has been proposed (see Japanese Examined Patent Publication No. hei 6-95921, for example).

It is thinkable to apply a flavoring material onto cigarette wrapping paper instead of adding a flavoring material to cut tobacco or seam glue. A flavoring material is applied onto cigarette wrapping paper to improve the taste of cigarettes and/or suppress the odor of sidestream smoke. It is to be noted that in order to obtain a good taste of cigarettes by applying a flavoring material onto wrapping paper, the amount of the flavoring material applied onto the wrapping paper needs to be adjusted. In particular, when an odor-eliminating flavoring material capable of suppressing the odor of sidestream smoke is applied onto wrapping paper, the amount of the flavoring material applied needs to be adjusted more finely. Further, cigarettes made using that part of wrapping paper on which too small or too large an amount of a flavoring material is applied needs to be removed as defective products. In order to control the operation of a flavoring-material application device and a defective-product removal device to finely adjust the amount of a flavoring material applied and remove defective products, it is important to properly determine an applying state of the flavoring material applied on wrapping paper, as control information. It is however difficult to determine the applying state of the flavoring material.

Specifically, most flavoring materials are colorless, and therefore it is very difficult to determine the applying state of a flavoring material applied on wrapping paper through visual observation. Japanese Unexamined Patent Publication No. hei 4-34348 discloses a device for detecting defects due to non-uniformity of a sheet or the like such as a paper sheet or a polymeric film, using fluorescence radiated from a fluorescent substance. The principle of this inspection is that if a sheet or the like containing a fluorescent substance has structural non-uniformity in its surface or interior, light excited by the fluorescent reaction when the sheet or the like is illuminated by ultraviolet light is non-uniform. This non-uniform light is detected as indicating the existence of defects.

It is thinkable to apply such fluorescent reaction to the inspection on a flavoring material applied on cigarette wrapping paper. Specifically, it is thinkable to cast ultraviolet light onto wrapping paper on which a flavoring material containing a fluorescent substance or with a fluorescent substance added is applied, to cause fluorescence irradiation, and to determine an applying state of the flavoring material applied, by detecting the radiated fluorescence.

However, even if fluorescence radiated from a fluorescent substance contained in the flavoring material when illuminated by ultraviolet light can be detected, it only makes it possible to identify a region of wrapping paper in which the flavoring material is applied and determine whether or not there are defects in that region. It is difficult to inspect an applying state of the flavoring material applied, precisely enough to determine whether cigarettes are defective or not.

DISCLOSURE OF THE INVENTION

An object of the invention is to provide an applied flavoring-material inspecting device suitable to inspect an applying state of a flavoring material applied on cigarette wrapping paper.

Another object of the invention is to provide a cigarette making machine provided with an applied flavoring-material inspecting device for inspecting an applying state of a flavoring material applied on cigarette wrapping paper.

In order to establish an inspection technique for determining an applying state of a flavoring material applied on wrapping paper using fluorescent reaction, the inventors observed fluorescence radiated when ultraviolet light was cast onto wrapping paper on which a flavoring material containing a fluorescent substance was applied, under various conditions. Specifically, a flavoring material containing a fluorescent substance or with a fluorescent substance added was linearly applied onto a long strip of wrapping paper used for making cigarettes; an image of an imaging region with a predetermined area preset for the wrapping paper was obtained by a camera from radiated fluorescence when ultraviolet light was cast onto the surface of the wrapping paper on which the flavoring material was applied; and irradiation intensity distribution in the image was obtained. Using different types of flavoring materials (specifically, flavoring materials containing a different fluorescent substance or with a different fluorescent substance added) and changing the amount of the flavoring material applied and others, this experiment was repeated, so that relation between the amount of the flavoring material applied and the irradiation intensity distribution was obtained for different types of flavoring materials. As a result, it showed that there is a correlation between the amount of the flavoring material applied on the cigarette wrapping paper and the irradiation intensity distribution in the image, and that there is a particularly distinctive correlation between the amount of the flavoring material applied and the width of a specific zone of the image (the zone of the image which has pixels with an irradiation intensity greater than a predetermined intensity, hereinafter referred to also as "fluorescence irradiation zone). Specifically, it was recognized that between the amount of the flavoring material applied and the irradiation intensity, there is relation shown in FIGS. 1A and 1B. In the figures, symbols P, F and D0 represent a wrapping paper, a flavoring material and the width in which the flavoring material is applied, respectively. Symbols D1 and D2 each represent the width of the above-mentioned specific zone.

Figure 1A:
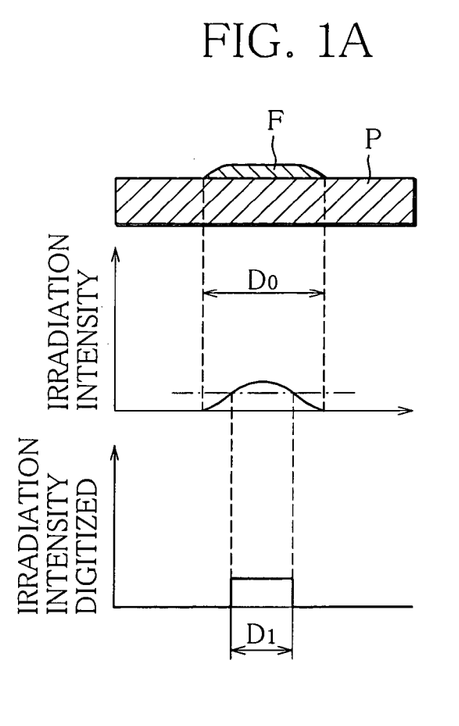
FIG. 1A is a diagram showing relation between the amount of a flavoring material containing a fluorescent substance or with a fluorescent substance added, applied onto wrapping paper and irradiation intensity distribution in an image of the wrapping paper obtained from fluorescence radiated when ultraviolet light is cast onto the wrapping paper.
Figure 1B:
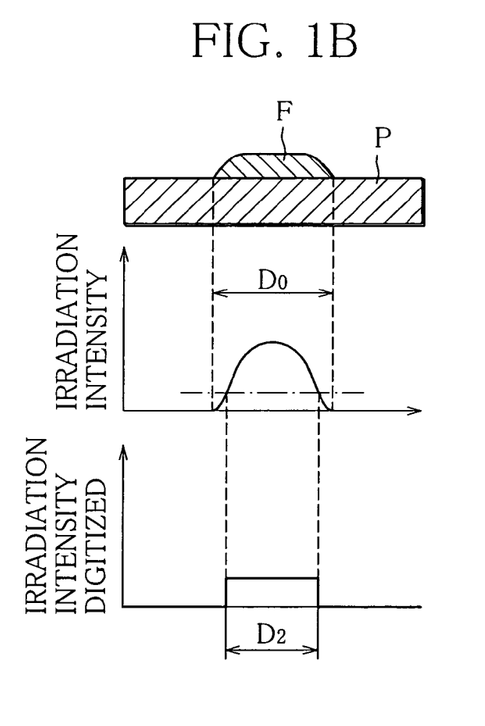
FIG. 1B is a diagram showing a relation between the amount of the flavoring material applied and the irradiation intensity distribution obtained when the amount of the flavoring material applied is increased.

In the experiment to which FIGS. 1A and 1B relate, a flavoring material F with a fluorescent substance added or containing a fluorescent substance was applied onto the wrapping paper P in a predetermined width, and ultraviolet light was cast onto the surface of the wrapping paper P on which the flavoring material was applied, before the flavoring material F infiltrated into the wrapping paper P (for example, within about 5 seconds after the flavoring material was applied). An image signal from the camera was digitized by comparing the brightness of each pixel with a predetermined threshold value, and the widths D1 and D2 of the fluorescence irradiation zones having pixels with a brightness greater than the threshold value were obtained. In the experiment to which FIGS. 1A and 1B relate, the amount of the flavoring material applied was larger in the instance shown in FIG. 1B than in the instance shown in FIG. 1A, while the width D0 in which the flavoring material was applied was the same. Because of this, the irradiation intensity in the image was stronger in the instance shown in FIG. 1B than in the instance shown in FIG. 1A, and the width of the fluorescence irradiation zone was larger in the instance of FIG. 1B (D2>D1). It is inferred that this comes from the difference in the thickness of the flavoring material F on the wrapping paper P, which difference is caused by the difference in the amount of the flavoring material applied.

Further, the inventors calculated the area of the fluorescence irradiation zone in the image and obtained relation between the area of the fluorescence irradiation zone and the amount of the flavoring material applied. Specifically, a series of images of the wrapping paper on which a known amount of a flavoring material was applied was successively obtained by a camera, the width of the fluorescence irradiation zone in each image was obtained, and then the width of this zone times the known length of the fluorescence irradiation zone, namely the area of the fluorescence irradiation zone was obtained. Further, by adding the areas of all the fluorescence irradiation zones together, the total area of fluorescence irradiation zones in the series of images was obtained. Under different experimental conditions where different fluorescence substances were used and the amount of the flavoring material applied was changed, the total area of fluorescence irradiation zones were calculated in the same way.

Figure 2:
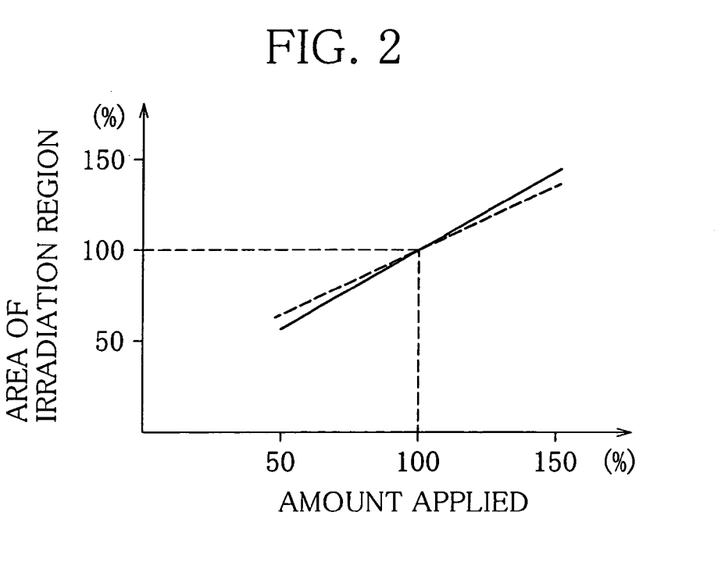
FIG. 2 is a diagram showing relation between the amount of a flavoring material applied and the area of an fluorescence irradiation region, regarding two instances where the fluorescent substance used is different.

FIG. 2 shows the relation between the total area of fluorescence irradiation zones, which was calculated this way, and the amount of the flavoring material applied, which was known. The relation was obtained for two instances where different fluorescent substances were used, which are indicated by a solid line and a broken line, respectively. In the figure, the total area of fluorescence irradiation zones and the amount of the flavoring material applied are expressed in percentage (%) relative to the typical area and amount. As seen from FIG. 2, the total area of fluorescence irradiation zones is almost proportional to the amount of the flavoring material applied.

As stated above, the experiment showed that there is a correlation between the amount of the flavoring material applied on the cigarette wrapping paper (more generally, an application state of the flavoring material applied) and the fluorescence irradiation intensity distribution in the image, and that there is a particularly distinctive correlation between the width of the fluorescence irradiation zone and the amount of the flavoring material applied. On the basis of this knowledge, the inventors made the present invention.

In one form, the invention provides an applied flavoring-material inspecting device for inspecting an applying state of a flavoring material applied on cigarette wrapping paper, comprising a light source for casting ultraviolet light onto a flavoring-material applied surface of cigarette wrapping paper on which a flavoring material with a fluorescent substance added or containing a fluorescent substance is applied; a camera for obtaining an image of the flavoring-material applied surface from fluorescence radiated due to the ultraviolet light; image processing means for obtaining information correlative to an application state of the flavoring material applied on the cigarette wrapping paper, from fluorescence irradiation intensity distribution in the image; and determination means for determining the applying state of the flavoring material applied on the cigarette wrapping paper on the basis of the information correlative to the application state of the flavoring material.

This invention is based on the knowledge that when an image of wrapping paper, on which a flavoring material containing a fluorescent substance or with a fluorescent substance added is applied, is obtained from fluorescence radiated by casting ultraviolet light onto the wrapping paper, there is found a correlation between fluorescence irradiation intensity distribution in the image and an application state of flavoring material applied on the wrapping paper. Therefore, this invention is attained by determining an applying state of the flavoring material applied on the basis of the information correlative to the application state of the flavoring material, the information being obtained from the fluorescence irradiation intensity distribution. Thus, by using the fluorescent reaction, the applying state of the flavoring material applied on the wrapping paper can be inspected reliably and easily. Further, by using the information obtained in this inspection as control information for controlling an flavoring-material application device provided in a cigarette making machine, it is possible to control the application of the flavoring material onto the wrapping paper by the flavoring-material application device, in a good manner, to control the applying state of the flavoring material. Therefore, it is possible to produce cigarettes having a good taste, particularly cigarettes capable of suppressing the odor of sidestream smoke.

In the present invention, desirably, the camera successively obtains a series of images of an inspection region preset for the cigarette wrapping paper; the image processing means detects a fluorescence irradiation zone having fluorescence irradiation intensities greater than a predetermined value, from fluorescence irradiation intensity distribution in each of the images; and the determination means identifies a flavoring-material application region of the wrapping paper, from the fluorescence irradiation zone detected in each of the images. In this desirable mode, from the fluorescence irradiation zone detected in each of the images, a flavoring-material application region can be identified in an inspection region in each image of the wrapping paper, and therefore, whether or not the flavoring-material application region is present in an inspection region and whether or not the flavoring-material application region has a break can be determined.

More desirably, the image processing means detects, from the fluorescence irradiation intensity distribution in each of the images, the width of the fluorescence irradiation region in each of the images as information correlative to the application state of the flavoring material, and further obtains the area of the fluorescence irradiation region in each of the images, on the basis of the width of the fluorescence irradiation region in each of the images. Further, the determination means determines the amount of the flavoring material applied, on the basis of the total of the areas of the fluorescence irradiation regions in the images. There is a distinctive correlation between the width of the fluorescence irradiation region detected in each of the images and the amount of the flavoring material applied. Further, there is a distinctive correlation between the total of the areas of the fluorescence irradiation regions in the images and the amount of the flavoring material applied. Therefore, in this desirable mode, the amount of the flavoring material, which well indicates the applying state of the flavoring material, can be determined precisely, and the applying state of the flavoring material can be inspected reliably.

Desirably, the flavoring material is applied linearly along the length of the cigarette wrapping paper, and the camera obtains a series of images of an inspection region set for the cigarette wrapping paper so as to widthwise cover the part of the cigarette wrapping paper in which the flavoring material is applied. In this desirable mode, the applying state of the flavoring material can be inspected over all that part of the wrapping paper in which the flavoring material is applied. The applying state of the flavoring material applied on the wrapping paper therefore can be inspected reliably.

In another form, the present invention provides a cigarette making machine, comprising a wrapping section for wrapping cut tobacco in cigarette wrapping paper; an application device for applying a flavoring material onto a flavoring-material application surface of the wrapping paper; and an applied flavoring-material inspecting device for inspecting an applying state of the flavoring material applied on the cigarette wrapping paper, wherein the applied flavoring-material inspecting device includes a light source for casting ultraviolet light onto the flavoring-material application surface of the cigarette wrapping paper on which the flavoring material with a fluorescent substance added or containing a fluorescent substance is applied; a camera for obtaining an image of the flavoring-material application surface from fluorescence radiated due to the ultraviolet light; image processing means for obtaining information correlative to an application state of the flavoring material applied on the cigarette wrapping paper, from fluorescence irradiation intensity distribution in the image; and determination means for determining an applying state of the flavoring material applied on the cigarette wrapping paper, on the basis of the information correlative to the application state of the flavoring material, and the camera of the applied flavoring-material inspecting device and the application device are located in a stage prior to the wrapping section.

In this invention, an applying state of the flavoring material applied on the cigarette wrapping paper to be fed to the wrapping section can be controlled well. Thus, the invention can provide a cigarette making machine suitable to make cigarettes having a good taste, particularly cigarettes capable of suppressing the odor of sidestream smoke.

Desirably, the cigarette wrapping paper includes an inner wrapper for wrapping cut tobacco therein and an outer wrapper for being wrapped around the inner wrapper, and the application device applies the flavoring material onto the inner surface of the outer wrapper which forms the flavoring-material application surface of the cigarette wrapping paper.

In this desirable mode of the cigarette making machine, the flavoring material is applied onto the inner surface of the outer wrapper of the cigarette wrapping paper (the surface of the outer wrapper which faces the inner wrapper). Therefore, cigarettes capable of suppressing the odor of sidestream smoke without affecting the taste of the cigarettes can be produced. Specifically, by applying an odor-eliminating flavoring material capable of suppressing the odor of sidestream smoke onto the outer wrapper, the flavoring material produces the odor elimination effect better, compared with when such flavoring material is added to cut tobacco, for example, and the odor of sidestream smoke can be suppressed well. In addition, the inner wrapper sandwiched between the outer wrapper and cut tobacco prevents the flavoring material from entering mainstream smoke when the cigarette is smoked. Therefore, for example the concern that the effect of another flavoring material added to cut tobacco to improve the taste is damaged is reduced. Further, compared with when the flavoring material is added onto the outer surface of the outer wrapper, the change in the state of the flavoring material applied on the outer wrapper with time can be reduced, and the concern that the cigarette deteriorates in appearance can be reduced.

Desirably, the camera of the applied flavoring-material inspecting device is located downstream from the application device in a feeding path along which the cigarette wrapping paper is fed to obtain an image of the flavoring-material application surface of the wrapping paper immediately after the flavoring material is applied. More desirably, the camera and the application device is separated by a distance corresponding to a predetermined time shorter than the time taken for the flavoring material applied onto the cigarette wrapping paper to infiltrate into the cigarette wrapping paper or the time taken for volatile constituents of the flavoring material applied onto the cigarette wrapping paper to evaporate from the flavoring material. In these desirable modes, an applying state of the flavoring material applied, particularly an amount of the flavoring material applied can be inspected reliably, before the flavoring material infiltrates into the wrapping paper or before the volatile constituents thereof evaporates.

Desirably, the cigarette making machine includes an applied amount control section for controlling the amount of the flavoring material to be applied by the application device, depending on inspection data about an applying state of the flavoring material applied on the cigarette wrapping paper, the inspection data being supplied by the determination means of the applied flavoring-material inspecting device. In this desirable mode, the amount of the flavoring material applied onto the wrapping paper can be controlled well.

Desirably, the cigarette making machine can remove a cigarette formed with that part of the cigarette wrapping paper about which the determination means of the applied flavoring-material inspecting device has determined that the flavoring material is not applied properly, in accordance with a defective-product removal signal which the determination means sends out when the determination means determines that the flavoring material is not applied properly. In this desirable mode, a cigarette formed with the defective part of the wrapping paper can be removed reliably.

Desirably, the camera of the applied flavoring-material inspecting device obtains an image of the flavoring-material application surface of the cigarette wrapping paper, in synchronization with controlled operation of the cigarette making machine. In this desirable mode, control on the application of the flavoring material onto the wrapping paper and the removal of a cigarette formed with a defective part of the wrapping paper can be properly performed on the basis of the information about an applying state of the flavoring material applied, at a timing in harmony with a timing at which the operation of the cigarette making machine is controlled.

BEST MODE OF CARRYING OUT THE INVENTION

Referring to the drawings, an applied flavoring-material inspecting device as an embodiment of this invention will be described.

Figure 3:
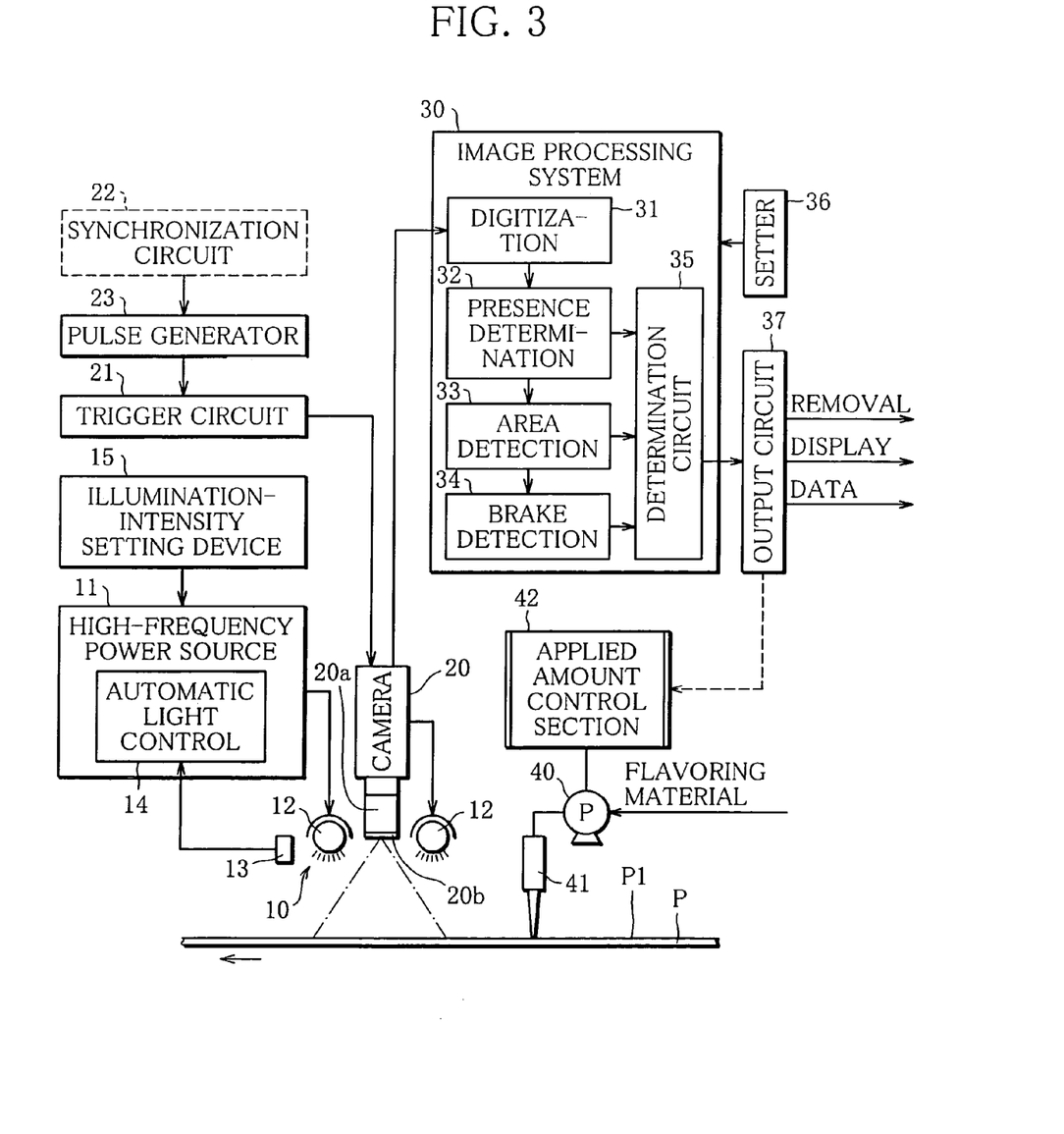
FIG. 3 is a schematic diagram showing the structure of an applied flavoring material inspecting device as an embodiment of this invention.

This applied flavoring material inspecting device is, for example incorporated into a cigarette making machine to inspect an applying state of a flavoring material applied on wrapping paper P used for making cigarettes. As shown in FIG. 3, the applied flavoring material inspecting device includes a light source 10 for casting ultraviolet light onto a flavoring-material application surface of the wrapping paper P on which a flavoring material is applied, a camera 20 for obtaining an image of the flavoring-material application surface of the wrapping paper P illuminated by the light source 10, and an image processing device 30 for processing an image obtained by the camera 20.

The flavoring material applied onto the wrapping paper P is one for alleviating or masking odor produced when cigarettes are smoked, particularly the odor of sidestream smoke. The flavoring material comprises one or more substances selected from a group consisting of terpenes, esters, alcohols such as linalool, nerol and geraniol, phenols such as anethole, aldehydes such as vanillin and ethyl vanillate, lactones, plant extracts, fruit extracts, and others. The flavoring material may be any of materials as disclosed in Japanese Unexamined Patent Publication No. 2002-146386.

The flavoring material may be one in liquid form and containing a fluorescent substance as its constituent, or a fluorescent substance may be added to the flavoring material. As the fluorescent substance added to the flavoring material, for example methyl anthoranilate or orange peel essential oil can be used, where fluorescent benzyl alcohol or the like can be used as a solvent.

The flavoring material containing a fluorescent substance as mentioned above is supplied to an application nozzle 41, for example by a pump 40 and linearly applied onto the flavoring-material application surface P1 of the wrapping paper P. The application nozzle 41 is located to a wrapping-paper travelling path which extends from a roll (not shown) to a wrapping section (not shown) of a cigarette making machine. Although in the present embodiment the application nozzle 41 is used as a device for applying the flavoring material, the flavoring material may be applied using a roller.

The application nozzle 41 has an end which contacts a widthwise central part of the flavoring-material application surface P1 of the wrapping paper P, and the flavoring material forced out of this nozzle end is put on the flavoring-material application surface. By forcing the flavoring material out of the nozzle end while the wrapping paper P is travelling, the flavoring material is applied onto the flavoring-material application surface P1 of the wrapping paper and forms a line of a predetermined width continuing along the length of the wrapping paper. The amount of the flavoring material applied is optimized by controlling the operation of the pump 40 by an applied amount control section 42, as will be described later. The wrapping paper P with the flavoring material applied on is fed to the wrapping section of the cigarette making machine and used to wrap cut tobacco therein. It is to be noted that although in the example described here, the flavoring material is applied onto the wrapping paper P to form a single line, the flavoring material may be so applied as to form two or more lines widthwise separated from each other by a predetermined distance.

The light source 10 includes an ultraviolet lamp 12 as the main part thereof, the lamp 12 is driven by a high-frequency power source 11 to cast ultraviolet light (at wavelengths from 300 to 400 nm, for example). The light source 10 further includes a photo detector 13 for detecting the intensity (amount) of ultraviolet light cast from the ultraviolet lamp 12, and automatic light control means 14 for drive-controlling the high-frequency power supply 11 depending on the amount of light detected by the photo detector 13 to keep the intensity of ultraviolet illumination by the ultraviolet lamp 12 constant. The light control by the automatic light control means 14 is performed to keep the intensity of illumination at a value set by an illumination-intensity setting device 15 to thereby ensure that the wrapping paper P is illuminated at a constant intensity of illumination. The light source 10 is not limited to the one shown here by way of example, as long as the light source 10 can illuminate the flavoring-material application surface P1 of the wrapping paper P with ultraviolet light.

The camera 20 for obtaining an image of the flavoring-material application surface P1 of the wrapping paper P is a small-sized one using solid-state image sensing devices such as CCDs. This camera 20 is actuated at predetermined timings by a trigger circuit 21, and controlled to successively obtain images of a predetermined length of the flavoring-material application surface P1 of the continuously travelling wrapping paper P. The imaging range of the camera 20 is set, for example as a rectangular region of which the sides parallel to the width of the wrapping paper P is longer than the overall width of the wrapping paper and the sides parallel to the length of the wrapping paper P has a predetermined length (see FIG. 4A). Specifically, when the overall width of the wrapping paper P is 30 mm, the imaging range of the camera 20 is set as a rectangular region of which the sides parallel to the width of the wrapping paper are 34 mm long and the sides parallel to the length of the wrapping paper are 36 mm long. The camera 20 is so arranged as to obtain an image of the flavoring-material application surface of the wrapping paper P, with a linear flavoring-material application region located in the center of the image. Further, the camera has a polarizing filter 20b mounted in front of its imaging lens 20a to obtain an image in which fluorescence radiated from the flavoring material exposed to ultraviolet light is emphasized.

This inspecting device is adapted to inspect an applying state of the flavoring material applied on wrapping paper P, on the basis of the images of the wrapping paper P onto which the flavoring material was applied by the application nozzle 41, obtained by the camera 20. In order to perform this inspection in a good manner, it is desirable to obtain images of the flavoring-material application surface P1 by the camera 20 before the flavoring material applied onto the flavoring-material application surface P1 of the wrapping paper P infiltrates into the wrapping paper P or before the volatile constituents of the flavoring material evaporates from the flavoring material. Therefore, in the present embodiment, in order to perform the inspection in a good manner, the camera 20 is located downstream from the application nozzle 41, separated from the application nozzle 41 by a short distance corresponding to a predetermined time which is shorter than the time taken for the flavoring material applied onto the wrapping paper by the application nozzle 41 to infiltrate into the wrapping paper or the time taken for the volatile constituents of the flavoring material to evaporate from the flavoring material. Although this predetermined time varies depending on the type of wrapping paper, the type of flavoring material, the speed at which the wrapping paper travels, and others, the time is generally 5 seconds or shorter, and in some cases 0.02 to 0.5 seconds or shorter. The distance between the camera 20 and the application nozzle 41 is predetermined to correspond to the time predetermined this way.

The trigger circuit 21 for actuating the camera 20 is driven by a pulse generator 23 which generates a predetermined pulse signal by receiving an output from a synchronization circuit 22 such as an encoder which generates the signal in synchronization with the operation of the cigarette making machine, and triggers the camera 20 in synchronization with the travelling of the wrapping paper P. Specifically, the trigger circuit 21 controls the camera 20 to image the wrapping paper P, in synchronization with the cutting for forming cigarettes of a predetermined length. The wrapping paper P is imaged at such imaging timings, successively, over a predetermined length, on the basis of positions at which the wrapping paper is cut at the later stage. The images obtained are used for the inspection on the flavoring material applied by means of image processing described below.

The image processing device 30 in the applied flavoring material inspecting device is materialized using a general-purpose image processor, and processes the images obtained by the camera 20 and inspects the flavoring material applied. The image processing device 30 has a digitization function 31, namely a function of digitizing an image obtained by the camera 20 using a predetermined threshold value to obtain an image for inspection, a presence determination function 32, namely a function of determining whether or not a flavoring-material application region is present in the image for inspection, an area detection function 33, namely a function of detecting the size of the flavoring-material application region, and a break detection function 34, namely a function of detecting a break in the flavoring-material application region. By a determination circuit 35 comprehensively evaluating the information obtained by these determination and detection functions 32, 33 and 34, whether the flavoring material is properly applied or not is determined.

The threshold value used in digitization is set by a setter 36 depending on inspecting specifications, more specifically the optimum applied amount for the flavoring material, which will be described later. The evaluation of an applying state of the flavoring material applied, which is produced by the evaluation circuit 35, is supplied to an external device through an output circuit 37, for example in the form of a defective-product removal signal to the cigarette making machine, or an alarm display about a defective product. Further, the evaluation is supplied to a personal computer (not shown) or the like as inspection data, and also fed back to the applied amount control section 42 as applied amount control data.

Figure 4A:
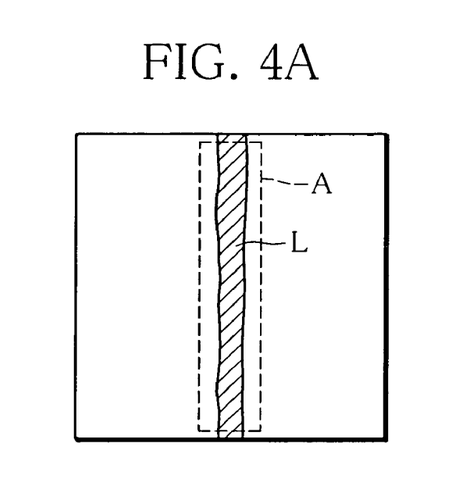
FIG. 4A is a diagram showing a first inspection region set in an image for inspection of a flavoring-material application surface of wrapping paper by the applied flavoring material inspecting device shown in FIG. 3.
Figure 4B:
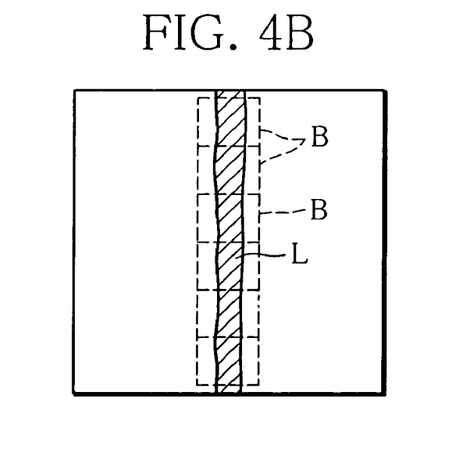
FIG. 4B is a diagram showing second inspection regions set in an image for inspection.

As shown in FIG. 4A, in the image for inspection obtained by the digitization function 31 of the image processing device 30, a first inspection region A is set to cover a flavoring-material application region L appearing in the image for inspection. Further, as shown in FIG. 4B, a plurality, for example 6 of second inspection regions B into which the region A is lengthwise divided are set in the image for inspection. Specifically, when the flavoring material is applied onto the wrapping paper P of 30 mm in width to describe a single line of about 3 mm in width in its central part, the first inspection region A is set as a 6 mm×36 mm rectangular region located in a central part of an image for inspection to cover the flavoring-material application region. The second inspection regions are set as 6 mm×6 mm regions. As described below, the applying state (the presence of the flavoring-material application region, the area (size) thereof, and the presence of a break therein) of the flavoring material is inspected for each of the first and second inspection regions A and B.

By the presence determination function 32 of the image processing device 30, a region L radiating fluorescence due to ultraviolet light (fluorescence irradiation region showing fluorescence irradiation intensities greater than the threshold value in digitization) in each of the first and second inspection regions A and B is identified as the flavoring-material application region. By the area detection function 33, the area of the fluorescence irradiation region L in each of the first and second inspection regions A and B is obtained by counting pixels in the fluorescence irradiation region L. Further, according to the break detection function 34, whether or not the flavoring material application region has a break is determined by inspecting the continuity of the fluorescence irradiation regions L along the length of the wrapping paper, particularly by inspecting that each of the second inspection regions B includes a predetermined area or an area larger than that of the fluorescence irradiation region L.

The determination circuit 35 detects excess or deficiency of the flavoring material applied in a region of the wrapping paper P that corresponds to one image for inspection, for example by obtaining the ratio (proportion) of the number of pixels contained in the fluorescence irradiation region L to the number of pixels contained in the first inspection region A, and also detects local variation in the amount of the flavoring material applied and local excess or deficiency thereof by obtaining the ratio (proportion) of the number of pixels contained in the fluorescence irradiation region L to the number of pixels contained in each second inspection region B. By comprehensively evaluating the information thus obtained, the determination circuit 35 determines whether or not the flavoring material is applied on the wrapping paper P in a proper manner (in a proper amount). When excess or deficiency of the flavoring material applied or a break in the linear application region is detected, a removal signal is output in order to remove cigarettes wrapped in that part of the wrapping paper P in which such excess, deficiency or a break has been detected.

After that part of the wrapping paper P on which the applied flavoring-material inspection has been performed is supplied to wrap cut tobacco therein, the removal signal is given to a removal section, according to the timing that a cigarette rod formed with that part of the wrapping paper is cut into a predetermined length. By this removal control, cigarettes wrapped in that part of wrapping paper in which the flavoring material is not applied in a proper amount and in a proper manner are removed as defective products from among cigarettes continuously produced, to guarantee the quality of cigarettes.

Further, the amount of the flavoring material applied obtained from the area of the fluorescence irradiation region L is fed back to the applied amount control section 42 for use in controlling the amount of the flavoring material supplied to the application nozzle 41 by the pump 40. By controlling the amount of the flavoring material supplied, the amount of the flavoring material applied onto the wrapping paper P by the application nozzle 41 is made constant.

The applied flavoring material inspecting device materialized as described above uses the phenomenon that the fluorescent substance contained in the flavoring material applied on the wrapping paper P radiates fluorescence when illuminated by ultraviolet light. This device can detect the area of the fluorescence irradiation region L in an image for inspection which is obtained by digitizing an image formed from the fluorescence radiated, by comparing pixels contained in this image with a predetermined threshold value. Further, by obtaining the amount of the flavoring material applied from the area of the fluorescence irradiation region L, this device can detect excess or deficiency of the flavoring material applied, and also detect easily a break in the flavoring-material application region. This produces beneficial effects such that quality control can be performed easily and effectively when a flavoring material is continuously applied onto a long strip of wrapping paper P and when cigarettes are produced using this wrapping paper P.

Next, as regards a cigarette making machine incorporating the above-described applied flavoring-material inspecting device, a cigarette making machine for making double-wrapped cigarettes will be described.

Figure 5:
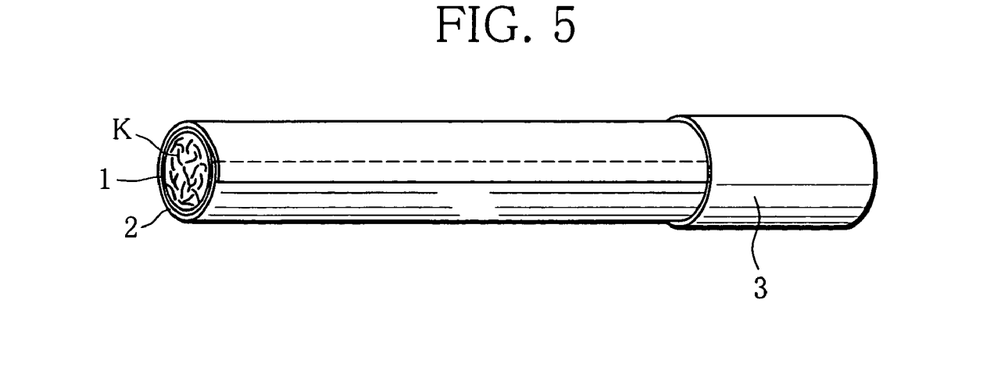
FIG. 5 is a diagram showing the appearance of a double-wrapped cigarette.
Figure 6:
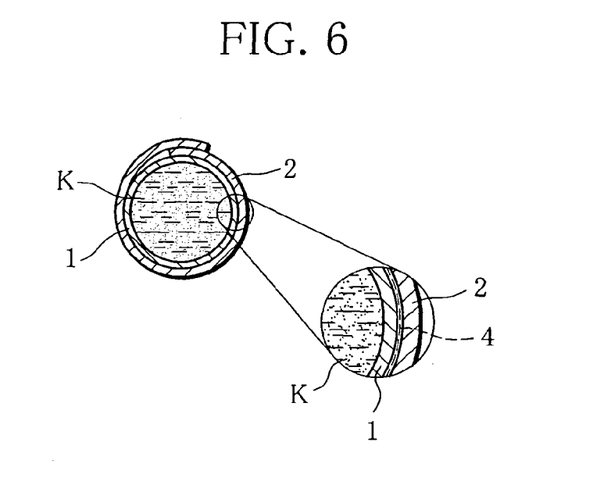
FIG. 6 is a diagram showing the cross-sectional structure of the double-wrapped cigarette.

As shown in FIG. 5, a double-wrapped cigarette is a cigarette in which cut tobacco (filler) K is wrapped in an inner wrapper 1 to form a cylindrical rod, an outer wrapper 2 is wrapped around the inner wrapper 1 concentrically, and a filter tip is attached to an end of the rod. As schematically shown in FIG. 6, the inner wrapper 1 has a width suited to wrap cut tobacco K therein, with its opposite sides met each other. The outer wrapper 2 has a width greater than that of the inner wrapper 1. The outer wrapper 2 wrapped around the inner wrapper 1 has its opposite sides which are laid on each other and bonded together by seam glue. Between the inner wrapper 1 and the outer wrapper 2, a flavor-emitting material 4 is arranged. The flavor-emitting material 4 is a mixture of a flavoring material as described above and a carrier such as glue, and applied, for example onto the inner wrapper 1 to completely or partially cover its outer surface, or onto the outer wrapper 2 to completely or partially cover its inner surface.

In order to suppress the odor of sidestream smoke, it is desirable to apply the flavor-emitting material 4 containing an odor-eliminating flavoring material capable of suppressing the odor of sidestream smoke onto the inner surface of the outer wrapper 2 (the surface of the outer wrapper 2 that faces the inner wrapper). In this case, it is possible to suppress the odor of sidestream smoke without affecting the taste of the cigarette. When such odor-eliminating flavoring material is applied onto the outer wrapper 2, the odor-eliminating flavoring material produces the odor-elimination effect better and therefore suppresses the order of sidestream smoke better, compared with when such flavoring material is added to cut tobacco, for example. In addition, the inner wrapper 1 arranged between the outer wrapper 2 and cut tobacco K prevents the fragrance from transferring mainstream smoke when the cigarette is smoked. Therefore, for example the concern that the effect of another flavoring material added to cut tobacco K to improve the taste is damaged is reduced. Further, compared with when the flavoring material is added onto the outer surface of the outer wrapper 2, change in the state of the flavoring material applied on the outer wrapper 2 with time can be reduced, and the concern that the cigarette deteriorates in appearance can be reduced.

The cut tobacco K is a mixture of cut tobacco obtained by cutting tobacco laminae and midribs, shreds obtained by cutting reconstituted sheet tobacco, and expanded cut tobacco obtained by expanding cut tobacco. The inner wrapper 1 and the outer wrapper 2 are made from flax pulp, wood pulp or other plant pulp with additives such as calcium carbonate or a magnesium compound added. The inner wrapper 1 and the outer wrapper 2 may contain a burning regulator such as an organic acid salt or an ash regulator such as a phosphoric acid.

Figure 7:
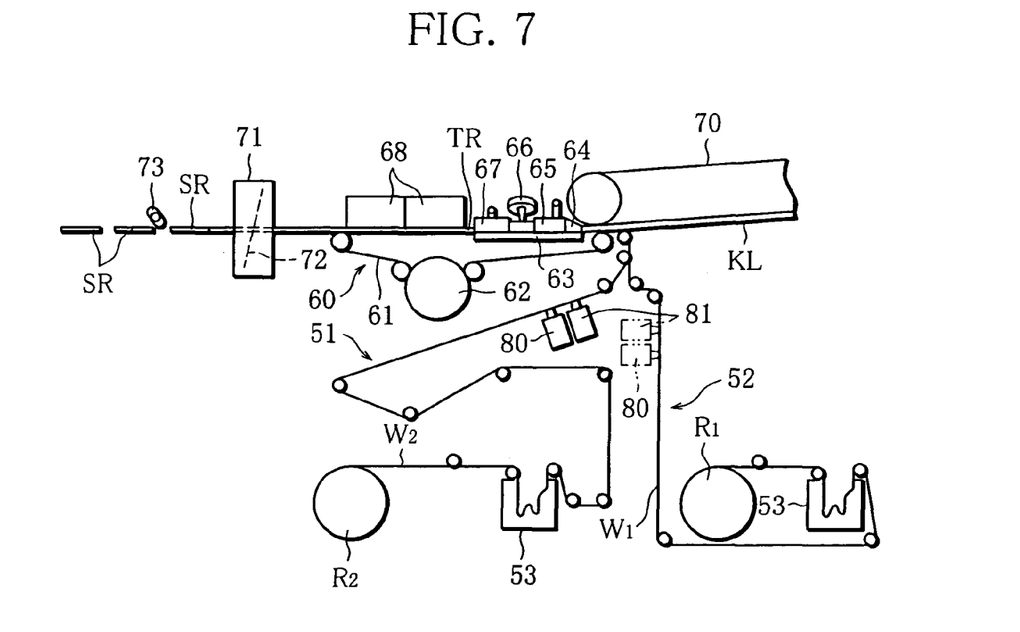
FIG. 7 is a diagram showing a schematic structure of a cigarette making machine incorporating an applied flavoring-material inspecting device.

A cigarette making machine for making the above-described double-wrapped cigarette is assembled as schematically shown in FIG. 7.

The making machine is provided with a roll R1 of wrapping paper W1 for the inner wrapper 1 and a roll R2 of wrapping paper W2 for the outer wrapper 2. The wrapping paper W1 and the wrapping paper W2 are let out from the roll R1 and the roll 2 along the feeding paths 51 and 52. The feeding paths 51 and 52 are defined by a plurality of guide rollers. The feeding paths 51 and 52 extend up to an inlet to a wrapping section 60. For each of the feeding paths 51 and 52, a feed roller (not shown) and a reservoir 53 are disposed along the path.

The wrapping section 60 has an endless garniture tape 61. Onto the garniture tape 61, the wrapping paper W1 and the wrapping paper W2 are successively fed from the terminal ends of the feeding paths 51 and 52. The wrapping paper W1 is laid on the wrapping paper W2 on the garniture tape 61 to form a double wrapper. The garniture tape 61 is extended to pass around a drive drum 62. As the drive drum 62 rotates, the garniture tape 61 travels in a forming groove (not shown) in a forming bed 63, with the double wrapper, in one direction. The forming groove in the forming bed 63 is so shaped that its width and the radius of curvature of its bottom gradually decrease from the inlet to the outlet of the wrapping section 60 so that the forming groove is approximately a semicircle in cross section at the outlet of the wrapping section 60.

At the inlet of the wrapping section 60, cut tobacco K is supplied onto the upper side of the wrapping paper W1 which forms the inner wrapper 1 of the double wrapper. More specifically, cut tobacco K is sucked onto the lower side of an endless tobacco band 70 to form a cut tobacco layer KL, and supplied to the inlet of the wrapping section 60 as the tobacco band 70 travels. The cut tobacco layer KL sucked on the tobacco band 70 is peeled from the tobacco band 70 by a tongue shoe 64 disposed at the inlet of the wrapping section 60 and transfers onto the wrapping paper W1 which forms the inner wrapper.

After supplied onto the wrapping paper W1 this way, the cut tobacco layer KL with the double wrapper passes through the wrapping section 60, more specifically through the tongue shoe 64, a short holder 65, a glue application nozzle 66 and a long holder 67, successively. While passing through the wrapping section, the cut tobacco K is wrapped in the double wrapper to form a continuous double-wrapped rod TR. The double-wrapped rod TR is delivered from the outlet of the wrapping section 60.

More specifically, the tongue shoe 64 compression-molds the cut tobacco layer KL from above into a circular arc in cross section, while the forming groove in the forming bed 63 bends the double wrapper from below into a U shape in cross section, with the garniture tape 21. Thus, the cut tobacco layer KL is compression-molded from above and from below, so that the upper and lower halves thereof are each formed into a circular arc in cross section. The short holder 65 bends a side part (first side part) of the double wrapper with the garniture tape 61 to describe an arc, and puts this first side part over a half of the upper half of the cut tobacco layer KL. At this time, the glue application nozzle 66 applies seam glue onto the other side part (second side part) of the wrapping paper W2 of the double wrapper. Then, the long holder 67 bends the second side part of the double wrapper with the garniture tape 61 to describe likewise an arc, and puts this second side part over the other half of the upper half of the cut tobacco layer KL. Thus, the second side part of the wrapping paper W2 overlaps the first side part thereof and is stuck to it with the seam glue. As a result, the double-wrapped tobacco rod TR is formed.

Then, while the tobacco rod TR delivered from the outlet of the wrapping section 60 passes under a heater 68, the seam glue is dried. Then, while passing through a cutting section 71, the tobacco rod TR is cut into cigarette rods SR of a predetermined length, namely twice the length of a double-wrapped cigarette, by a rotary knife 72 provided in the cutting section 60. The cigarette rods SR are supplied to the next stage, namely filter attachment (not shown), by a kicker 73.

In the filter attachment stage, each cigarette rod SR is cut into two double-wrapped cigarettes, then a filter plug is placed between these two double-wrapped cigarettes, then these two double-wrapped cigarettes with the filter plug therebetween are connected by wrapping a piece of tip paper around them to form a double filter cigarette, and then the double filter cigarette is divided equally to form filter cigarettes shown in FIG. 1.

According to the present embodiment, in the cigarette making machine basically arranged this way, a flavoring-material application device 80 including, for example an application nozzle 41 for applying a flavoring material onto wrapping paper W1 or W2 is arranged in the feeding path 51, downstream of the reservoir 53 as shown in FIG. 7. The flavoring-material application device 80 is adapted to apply a flavor-emitting material (flavoring-material) 4 in liquid form onto the inner surface of the wrapping paper W2, in a region except for the region in which seam glue is applied, or in a region of a predetermined width. At the inlet of the wrapping section 60, the flavoring material applied by the flavoring-material application device 80 forms a layer of the flavor-emitting material 4 between the wrapping paper W1 and the wrapping paper W2.

The flavor-emitting material 4 used here is a mixture of the flavoring material as mentioned above and a carrier such as EVA glue or PVAC glue used as seam glue. Therefore, the flavor-emitting material 4 functions as an adhesive for sticking the wrapping paper W1 and the wrapping paper W2 together. The PVAC glue has higher capacity to hold the flavoring material than the EVA glue and the CMC glue, and releases the fragrance better when the cigarette is smoked. As shown in FIG. 7, the applied flavoring-material inspecting device 81 according to the present invention is arranged downstream of the flavoring-material application device 80 to inspect an applying state of the flavoring material immediately after the flavoring-material application device 80 applies the flavor-emitting material 4 onto the wrapping paper W2.

Thus, in the cigarette making machine arranged as described above, while cigarettes are produced continuously, the applying state of the flavoring material applied on the wrapping paper W2 used for making the cigarettes can be inspected in real time. If the flavoring material is not applied properly, the cigarettes wrapped in such defective part of the wrapping paper can be removed quickly. Thus, the quality of cigarettes produced can be guaranteed stably.

The cigarette making machine is not restricted to that shown in FIG. 7. Various modifications can be made to it. For example, the flavoring-material application device 80 may form a layer having a plurality of streaks, on the inner surface of the wrapping paper W1. The present invention can be applied to the machine in which the flavoring-material application device 80 is located in the feeding path 52 as indicated in chain double-dashed lines. In this case, the flavoring-material application device 80 applies the flavor-emitting material on the outer surface of the wrapping paper W1. Further, the flavoring-material application devices 80 may be located in the feeding paths 51 and 52, respectively.

The flavoring-material application device 80 may be adapted to spray the flavor-emitting material in power form onto the wrapping paper W1 or W2. In this case, an adhesive is applied onto a surface of the wrapping paper W2, and then the flavor-emitting material in power form is sprayed onto the surface with the adhesive applied on. The flavor-emitting material in powder form may be a flavoring material such as dextrin or curdlan in power form, or a carrier such as β-cyclodedtrin carrying the flavoring material as mentioned above.

The present invention is not restricted to the above-described embodiment and modifications.

For example, in the embodiment described above, in order to suppress the odor of sidestream smoke, the double wrapper having an inner wrapper 1 and an outer wrapper 2 is used, and a flavor-emitting material 3 containing an order-eliminating flavoring material capable of suppressing the odor of sidestream smoke is applied onto the outer wrapper 2. The invention is however not restricted to this way of applying the flavoring material. For example, such odor-eliminating flavoring material or a flavoring material for improving the taste may be applied onto a single wrapper.

The threshold value used in digitizing images of the flavoring-material application surface should be set depending on the conditions in which the flavoring-material application surface is illuminated by ultraviolet light to obtain images and the fluorescence-irradiation characteristics of the fluorescent substance contained in the flavoring material. The imaging range of the camera 20 may be determined depending on the size of the inspection region and others. The resolution (resolving power) of the camera 20 may be selected depending on the inspecting specifications. In other respects, the present invention can be modified in various ways without departing from its spirit.

The invention claimed is:

1. An apparatus having an application device for applying a flavoring material onto a cigarette wrapping paper and an applied flavoring-material inspecting device for inspecting an applying state of the flavoring material applied on the cigarette wrapping paper, comprising:
   a feeding path for feeding the cigarette wrapping paper, the application device being arranged along the feeding path,
   a light source for casting ultraviolet light onto a flavoring-material application surface of cigarette wrapping paper on which a flavoring material with a fluorescent substance added or containing a fluorescent substance is applied,
   a camera for obtaining an image of the flavoring-material application surface from fluorescence radiated due to the ultraviolet light, said camera and said application device being separated from each other by a distance corresponding to a predetermined time shorter than time taken for the flavoring material applied onto the cigarette wrapping paper to infiltrate into the cigarette wrapping paper, image processing means for obtaining information correlative to an applied state of the flavoring material applied on the cigarette wrapping paper, from fluorescence irradiation intensity distribution in the image, and determination means for determining the applying state of the flavoring material on the cigarette wrapping paper, on the basis of the information correlative to the applied state of the flavoring material, said determination means being adapted to determine an amount of the flavoring material applied onto the cigarette wrapping paper, wherein the application device is adapted to apply the flavoring material with the fluorescent substance added or containing the fluorescent substance as its constituent onto the wrapping paper, wherein the flavoring material is a liquid, and the cigarette wrapping paper allows the flavoring material to infiltrate therein, wherein the light source and the camera are individually arranged along the feeding path on a downstream side of the application device at a predetermined distance from the application device, and wherein the distance is determined such that the wrapping paper on which the liquid flavoring material is applied by the application device passes by the light source and the camera before the applied flavoring material infiltrates into the wrapping paper, wherein the light source includes
an ultraviolet lamp for casting the ultraviolet light,
a photo detector for detecting intensity of the ultraviolet light radiated from the ultraviolet lamp onto the flavoring material application surface, and
a light controller operative in response to the intensity of the ultraviolet light detected by the photo detector to keep the intensity of the ultraviolet illumination on the flavoring material application surface constant.

2. The apparatus having an application device and the applied flavoring-material inspecting device according to claim 1, wherein
said camera obtains a series of images of an inspection region set for the cigarette wrapping paper in advance, successively,
said image processing means detects a fluorescence irradiation region having fluorescence irradiation intensities greater than a predetermined value, from fluorescence irradiation intensity distribution in each of the images, and
said determination means identifies a flavoring-material application region of the cigarette wrapping paper, from the fluorescence irradiation region detected in each of the images.

3. The apparatus having an application device and the applied flavoring-material inspecting device according to claim 2, wherein
said image processing means detects, from the fluorescence irradiation intensity distribution in each of the images, a width of the fluorescence irradiation region in each of the images as information correlative to the applied state of the flavoring material, and further obtains an area of the fluorescence emission region in each of the images, on the basis of the width of the fluorescence irradiation region in each of the images, and said determination means determines the amount of the flavoring material applied, on the basis of a total of the areas of the fluorescence irradiation regions in the images.

4. The apparatus having an application device and the applied flavoring-material inspecting device according to claim 3, wherein
the flavoring material is applied linearly along the length of the cigarette wrapping paper, and
said camera obtains a series of images of an inspection region set for the cigarette wrapping paper to widthwise cover the part of the cigarette paper in which the flavoring material is applied.

5. The apparatus having an application device and an applied flavoring-material inspecting device according to claim 1, wherein said camera of the applied flavoring-material inspecting device is located at a position in the feeding path which is downstream of said application device in order to obtain an image of the flavoring-material application surface of the wrapping paper immediately after the flavoring material is applied.

6. The apparatus having an application device and an applied flavoring-material inspecting device according to claim 1, further including an applied amount control section for controlling an amount of the flavoring material to be applied by said application device, depending on inspection data about the applying state of the flavoring material on the cigarette wrapping paper, the inspection data being supplied by said determination means of said applied flavoring-material inspecting device.

7. A cigarette making machine, comprising
a feeding path for feeding cigarette wrapping paper,
a wrapping section for wrapping cut tobacco in the cigarette wrapping paper,
an application device arranged along the feeding path for applying a flavoring material onto a flavoring-material application surface of the wrapping paper, and
an applied flavoring-material inspecting device for inspecting an applying state of the flavoring material applied on the cigarette wrapping paper, wherein
said applied flavoring-material inspecting device includes a light source for casting ultraviolet light onto the flavoring-material application surface of the cigarette wrapping paper on which the flavoring material with a fluorescent substance added or containing a fluorescent substance is applied;
a camera for obtaining an image of the flavoring-material application surface from fluorescence radiated due to the ultraviolet light; image processing means for obtaining information correlative to an application state of the flavoring material applied on the cigarette wrapping paper, from fluorescence irradiation intensity distribution in the image; said camera and said application device being separated from each other by a distance corresponding to a predetermined time shorter than time taken for the flavoring material applied onto the cigarette wrapping paper to infiltrate into the cigarette wrapping paper, and
determination means for determining the applied state of the flavoring material on the cigarette wrapping paper, on the basis of the information correlative to the application state of the flavoring material, said determination means being adapted to determine an amount of the flavoring material applied onto the cigarette wrapping paper, and said camera of said applied flavoring-material inspecting device and said application device are located in a stage prior to said wrapping section, wherein the application device is adapted to apply the flavoring material with the fluorescent substance added or containing the fluorescent substance as its constituent onto the wrapping paper, wherein the flavoring material is a liquid, and the cigarette wrapping paper allows the flavoring material to infiltrate therein, wherein the light source and the camera are individually arranged along the feeding path on a downstream side of the application device at a predetermined distance from the application device, and wherein the distance is determined such that the wrapping paper on which the liquid flavoring material is applied by the application device passes by the light source and the camera before the applied flavoring material infiltrates into the wrapping paper, an ultraviolet lamp for casting the ultraviolet light, a photo detector for detecting intensity of the ultraviolet light radiated from the ultraviolet lamp onto the flavoring material application surface, and a light controller operative in response to the intensity of the ultraviolet light detected by the photo detector to keep the intensity of the ultraviolet illumination on the flavoring material application surface constant.

8. The cigarette making machine according to claim 7, wherein the cigarette wrapping paper has an inner wrapper for wrapping cut tobacco therein and an outer wrapper for being wrapped around the inner wrapper, and said application device applies the flavoring material onto the inner surface of the outer wrapper which forms the flavoring-material application surface of the cigarette wrapping paper.

9. The cigarette making machine according to claim 7, wherein said camera of the applied flavoring-material inspecting device is located at a position in the feeding path which is downstream of said application device in order to obtain an image of the flavoring-material application surface of the wrapping paper immediately after the flavoring material is applied.

10. The cigarette making machine according to claim 7, further including an applied amount control section for controlling an amount of the flavoring material to be applied by said application device, depending on inspection data about the applying state of the flavoring material on the cigarette wrapping paper, the inspection data being supplied by said determination means of said applied flavoring-material inspecting device.

11. The cigarette making machine according to claim 7, wherein the cigarette making machine is adapted to remove a cigarette formed with that part of the cigarette wrapping paper about which said determination means of said applied flavoring-material inspecting device has determined that the flavoring material is not applied properly, according to a defective-product removal signal which said determination means outputs when said determination means determines that the flavoring material is not applied properly.

12. The cigarette making machine according to claim 7, wherein said camera of said applied flavoring-material inspecting device obtains an image of the flavoring-material application surface of the cigarette wrapping paper, in synchronization with controlled operation of the cigarette making machine.

* * * * *